(12) United States Patent
Wahl (10) Patent No.: US 12,178,483 B2
(45) Date of Patent: Dec. 31, 2024

(54) BONE PLATE WITH INSERT(S) FOR OPTIMALLY DIRECTING FASTENERS

(71) Applicant: In2Bones USA, LLC, Memphis, TN (US)

(72) Inventor: Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 218 days.

(21) Appl. No.: 17/728,552

(22) Filed: Apr. 25, 2022

(65) Prior Publication Data

US 2022/0257294 A1    Aug. 18, 2022

Related U.S. Application Data

(63) Continuation of application No. 15/015,995, filed on Feb. 4, 2016, now Pat. No. 11,311,323.

(60) Provisional application No. 62/113,313, filed on Feb. 6, 2015.

(51) Int. Cl.
*A61B 17/80* (2006.01)

(52) U.S. Cl.
CPC ...... *A61B 17/8047* (2013.01); *A61B 17/8057* (2013.01)

(58) Field of Classification Search
CPC .................................................. A61B 17/8047
See application file for complete search history.

(56) References Cited

U.S. PATENT DOCUMENTS

| 5,976,141 A | 11/1999 | Haag et al. |
| 6,331,179 B1 | 12/2001 | Freid et al. |
| 6,585,769 B1 | 7/2003 | Muhanna et al. |
| 6,613,053 B1 | 9/2003 | Collins et al. |
| 2004/0068319 A1 | 4/2004 | Cordaro |
| 2010/0274293 A1 | 10/2010 | Terrill et al. |
| 2013/0165980 A1* | 6/2013 | Cook ................. A61B 17/8047 606/286 |
| 2014/0222086 A1 | 8/2014 | Kuster |
| 2014/0324108 A1* | 10/2014 | Orbay ................ A61B 17/8061 606/289 |
| 2015/0335364 A1 | 11/2015 | Tacktill |

* cited by examiner

*Primary Examiner* — Olivia C Chang
(74) *Attorney, Agent, or Firm* — Rutan & Tucker LLP; Hani Z. Sayed (57) ABSTRACT

An apparatus is provided for fusing bones of the human body. The apparatus comprises a bone plate which generally is a member having one or more fixation apertures, configured to receive fasteners, and an insert aperture. The bone plate comprises a semi-rigid material, such as a biocompatible metal or Polyetheretherketone (PEEK), possessing a tensile strength suitable for immobilizing bones. A convertible insert is configured to be retained within the insert aperture. The convertible insert is configured to optimally direct a fastener towards a chosen point of purchase for fixating or compressing bones. In some embodiments, the insert is configured to direct a fastener at an oblique angle relative to a plane of the fusion plate. In some embodiments, the insert is configured to direct a fastener at a substantially right angle relative to the fusion plate.

12 Claims, 8 Drawing Sheets

BONE PLATE WITH INSERT(S) FOR OPTIMALLY DIRECTING FASTENERS

PRIORITY

This application claims the benefit of and priority to U.S. patent application Ser. No. 15/015,995 filed on Feb. 4, 2016 and U.S. Provisional Application, entitled "Bone Plate With Insert(s) For Optimally Directing Fasteners," filed on Feb. 6, 2015 having application Ser. No. 62/113,313.

FIELD

The field of the present disclosure generally relates to securing bones together. More particularly, the field of the present disclosure relates to an apparatus for fusing and compressing bones of the human body.

BACKGROUND

A fusion bone plate implant may be utilized in conjunction with one or more fasteners so as to generate compression and stability at a bone interface. An implant coupled with fasteners generally serves to stabilize bones, or bone parts, relative to one another so as to promote bone fusion. In many applications, bone plates and fasteners are used to fuse bones, or bone parts, of the human body, such as bones in the foot, the ankle, the hand, the wrist, as well as various other portions of the body. Furthermore, during the course of certain medical procedures, a surgeon may immobilize one or more bones or the bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus is provided for fusing bones of the human body. The apparatus comprises a bone plate which generally is a member having one or more fixation apertures, configured to receive fasteners, and an insert aperture. The bone plate comprises a semi-rigid material, such as a biocompatible metal or Polyetheretherketone (PEEK), possessing a tensile strength suitable for immobilizing bones. A convertible insert is configured to be retained within the insert aperture. The convertible insert is configured to optimally direct a fastener towards a chosen point of purchase for fixating or compressing bones. In some embodiments, the insert is configured to direct a fastener at an oblique angle relative to a plane of the fusion plate. In some embodiments, the insert is configured to direct a fastener at a substantially right angle relative to the fusion plate.

In an exemplary embodiment, an apparatus for fusing bones of the human body comprises a bone plate having one or more fixation apertures and one or more insert apertures; a convertible insert configured to be retained within the insert aperture, the insert being configured with a tapered, counter-bored, or countersunk internal shape to convert the direction of a fastener for fixating or compressing the bones; and one or more fixation screws configured to be received into the one or more fixation apertures and driven into the bones so as to fixate or compress the bones.

In another exemplary embodiment, the bone plate is comprised of a semi-rigid material, such as a biocompatible metal or Polyetheretherketone (PEEK), possessing a tensile strength suitable for immobilizing bones. In another exemplary embodiment, the convertible insert is configured to be press-fit into the insert aperture. In another exemplary embodiment, the convertible insert is configured to be mechanically retained within the insert aperture. In another exemplary embodiment, the insert aperture comprises a countersunk edge, the perimeter of which includes a round portion and a flat portion configured to orient the convertible insert to advantageously convert the fastener direction within the bone plate.

In another exemplary embodiment, the bone plate comprises a longitudinal rib and a multiplicity of lateral ribs, the longitudinal rib providing structural strength to the bone plate, the multiplicity of lateral ribs being configured to minimize contact between the implant and the bone. In another exemplary embodiment, the bone plate comprises a longitudinal rib and a multiplicity of radial ribs, the longitudinal rib inhibiting bending along a length of the bone plate, the multiplicity of radial ribs being configured to minimize contact between the bone plate and the bone, each radial ribs comprising a radius of curvature.

In another exemplary embodiment, the convertible insert is an insert comprising an aperture configured to receive a smooth headed fastener, such that the fastener is directed at an oblique angle relative to a plane of the fusion plate. In another exemplary embodiment, the oblique angle of the fastener facilitates compressing adjacent bones together so as to encourage bone fusion. In another exemplary embodiment, the insert aperture orients the insert, such that the fastener is directed at any angle between 0 to 360 degrees relative to the longitudinal implant axis so as to direct the fastener to an optimal point of bone purchase to successfully fuse the bone parts together.

In another exemplary embodiment, each of the fixation apertures comprises a countersunk or threaded surface configured to receive a head of the fastener, such that the fastener fixates the bone plate to the bones. In another exemplary embodiment, the convertible insert has an aperture configured to direct a fastener at a substantially right angle relative to the fusion plate. In another exemplary embodiment, the substantially right angle facilitates immobilizing adjacent bone of the human body. In another exemplary embodiment, the substantially right angle facilitates fixating bones across a joint.

In another exemplary embodiment, the insert aperture is configured to receive a circular insert comprising threads configured to engage with threads of the insert aperture. In another exemplary embodiment, the circular insert comprises an aperture configured to receive a smooth-headed screw, such that the fastener is directed at an oblique angle relative to a plane of the fusion plate. In another exemplary embodiment, the oblique angle facilitates compressing adjacent bones together so as to encourage bone fusion. In another exemplary embodiment, the insert threads orient the insert fastener relative to a longitudinal dimension of the fusion plate, thereby directing the fastener at an angle across a fusion site between the adjacent bones or an optimal point of bone purchase. In another exemplary embodiment, the angle ranges between substantially 0 degrees and 360 degrees relative to the longitudinal dimension of the fusion plate. In another exemplary embodiment, the circular insert comprises at least one engagement hole or peripheral slots configured to receive a distal protrusion of an insert driver, whereby the distal protrusion may be engaged into the engagement feature and the insert driver may be twisted so as to securely attach the circular insert within the insert aperture so as to direct the compression screw at the angle across a fusion site between the bones.

BRIEF DESCRIPTION OF THE DRAWINGS

The drawings refer to embodiments of the present disclosure in which.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first plate," may be made. However, the specific numeric reference should not be interpreted as a literal sequential order but rather interpreted that the "first plate" is different than a "second plate." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus for fusing bones of the human body. The apparatus comprises a bone plate which comprises a member having one or more fixation apertures and one or more insert apertures. The bone plate is comprised of a semi-rigid material, such as a biocompatible metal or Polyetheretherketone (PEEK), possessing a tensile strength suitable for immobilizing bones. A convertible insert is configured to be retained within the insert aperture. The insert is configured to direct a fastener towards an optimal point of bone purchase for fixating or compressing the bones. In some embodiments, the insert is configured to direct a fastener at a substantially right angle relative to the bone plate. Active compression between bones can be accomplished by driving the fastener through an elongated slot in the insert ramped on one side. It will be appreciated that the fastener shall have a smooth (non-threaded) head so that this movement within the insert slot may be achieved.

In some embodiments, the convertible insert is configured to direct a fastener at a substantially oblique angle to the bone plate. Fasteners are configured to be received into the one or more fixation apertures and driven into the bones so as to immobilize the bones. In some embodiments, the plate insert aperture is configured to receive a circular insert comprising threads configured to engage with threads of the insert aperture. The threads facilitate directing the insert fastener relative to a longitudinal axis of the fusion plate, in some instances directing the insert fastener at an angle across a fusion site between the adjacent bones and in some cases directing the fastener toward an optimal point of bone purchase. In some embodiments, the circular insert comprises at least one gripping hole configured to receive a distal protrusion of an insert driver. Engaging the distal protrusion into the gripping hole and twisting the insert driver facilitates rotating the circular insert within the insert aperture so as to attach the insert securely to the plate.

Figure 1A:
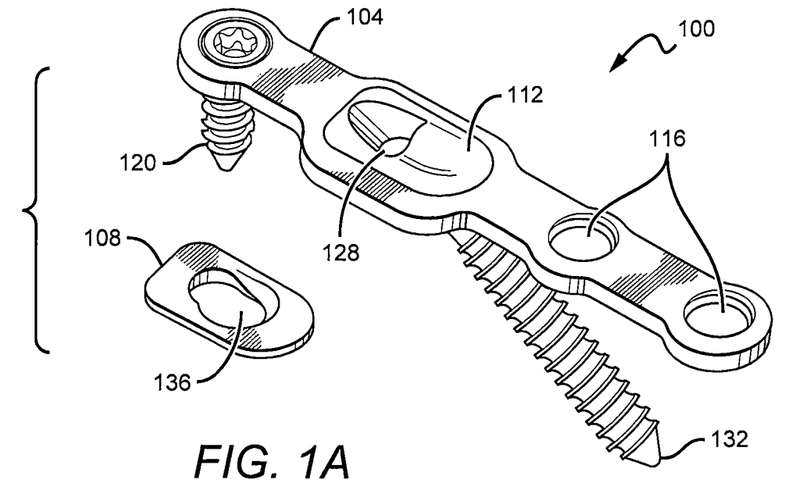
FIG. 1A illustrates an upper perspective view of an exemplary embodiment of a bone plate with two convertible inserts and a fastener, according to the present disclosure.
Figure 1B:
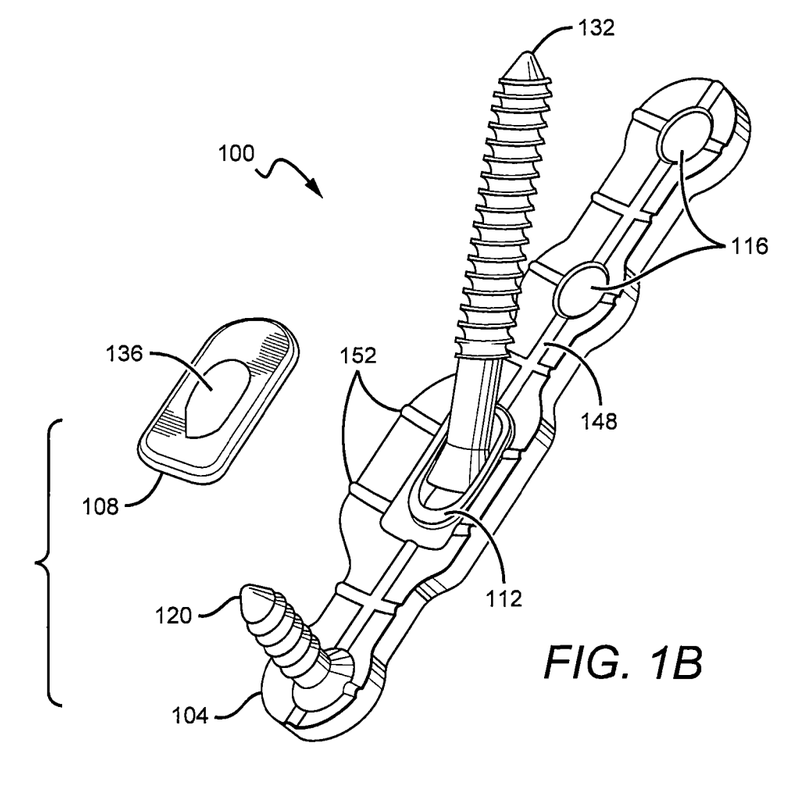
FIG. 1B illustrates a lower perspective view of an exemplary embodiment of a bone plate with a convertible insert and fastener in which the fastener is directed primarily in line with the longitudinal plate axis and oblique to a horizontal axis, and an additional insert that directs a fasteners primarily 90 degrees to a horizontal axis according to the present disclosure.

FIGS. 1A-1B illustrate an exemplary embodiment 100 of a bone plate 104 with a 90 degree fastener fixation insert 108 and an oblique fastener insert 112, according to the present disclosure. The bone plate 104 comprises a generally elongate member having fixation apertures 116 suitable for receiving fasteners 120. The bone plate 104 preferably is comprised of a semi-rigid material, such as a biocompatible metal or PEEK, possessing a tensile strength suitable for immobilizing adjacent bone parts of the human body.

As best illustrated in FIGS. 3A-4B, the bone plate 104 comprises an insert aperture 124 which is configured to receive either type of fixation insert 108,112. In the embodiment illustrated in FIGS. 1A-2B, the inserts 108 and 112 are configured to be pressed into the insert aperture 124. In some embodiments, however, the inserts 108 and 112 may be configured to be mechanically retained within the insert aperture 124, such as by way of non-limiting example, through an incorporation of threads, recesses, tabs, notches, clips, as well as various protruding formations, and other similar constructs.

As illustrated in FIGS. 1A-1B, the modular compression insert 112 comprises a convertible insert aperture 128 which is configured to receive a fastener 132, such that the threaded fastener 132 is directed at an oblique angle relative to a plane of the bone plate 104. The oblique angle of the fastener 132 facilitates compressing adjacent bones together so as to encourage bone fusion. The fastener 132 may be any component of hardware having a head configured to abut the surface of bone plate 104 and a shaft configured to secure bones together in a fixed configuration. In some embodiments, the fastener 132 may comprise a nut and bolt assembly, a pin assembly, a bone screw, or other similar fastener suitable for use in bone. In some embodiments, the fastener 132 may comprise a lag screw which includes a head that is rounded or tapered coupled to a shaft having an unthreaded portion adjacent to the head and a threaded portion that ends at a tip.

Figure 2A:
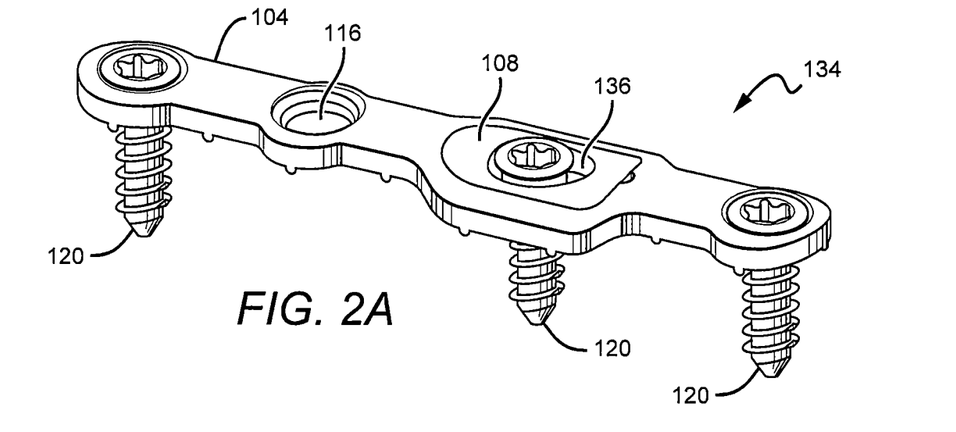
FIG. 2A illustrates an upper perspective view of an exemplary embodiment of a bone plate with a convertible insert in which the fastener is oriented primarily 90 degrees to a horizontal axis.
Figure 2B:
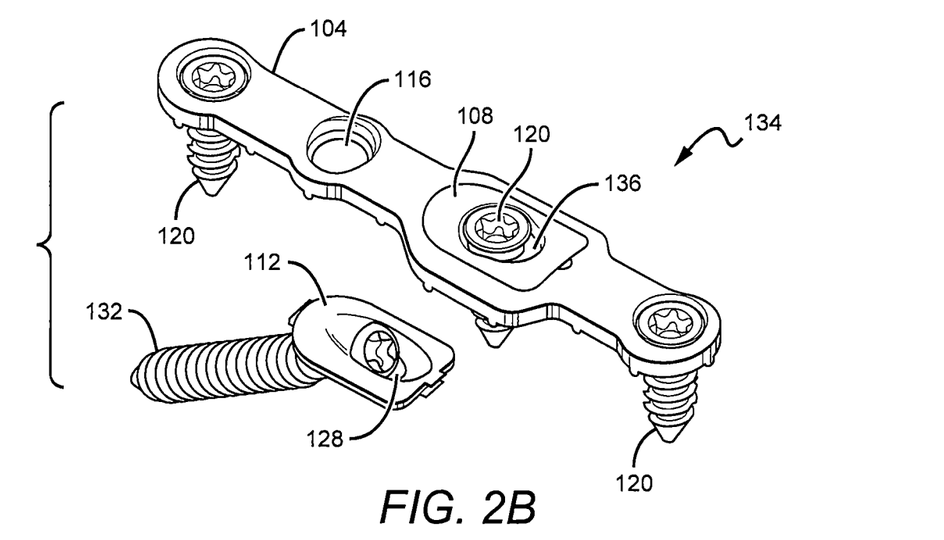
FIG. 2B illustrates the exemplary embodiment illustrated in FIG. 2A accompanied by a convertible insert configured for directing the fastener to a point of purchase in the bone that is approximately in line with plate long axis and oblique to horizontal axis, compressing bone parts in accordance with the present disclosure.
Figure 3A:
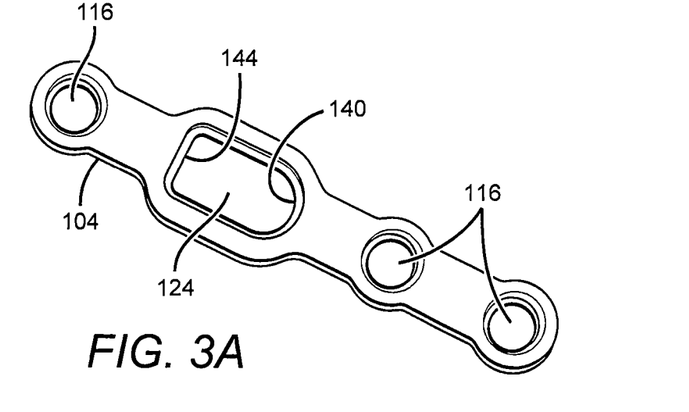
FIG. 3A illustrates an upper perspective view of an exemplary embodiment of a bone plate with an elongated aperture for the convertible washer, according to the present disclosure.
Figure 3B:
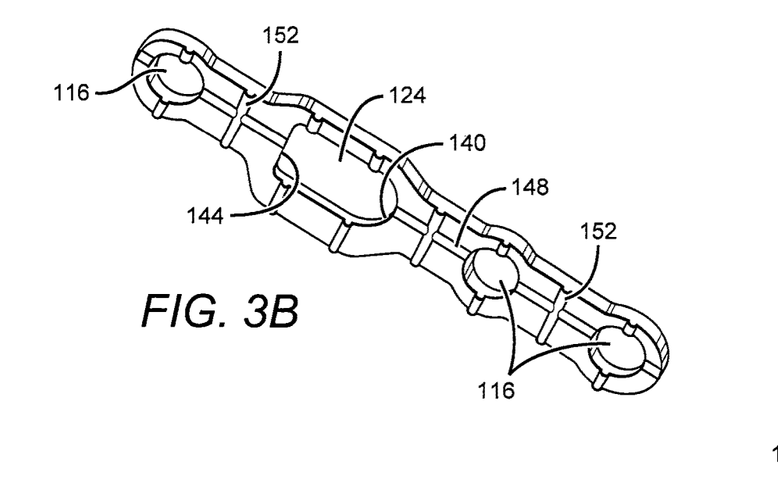
FIG. 3B illustrates a lower perspective view of the exemplary embodiment of FIG. 3A in accordance with the present disclosure.
Figure 4A:
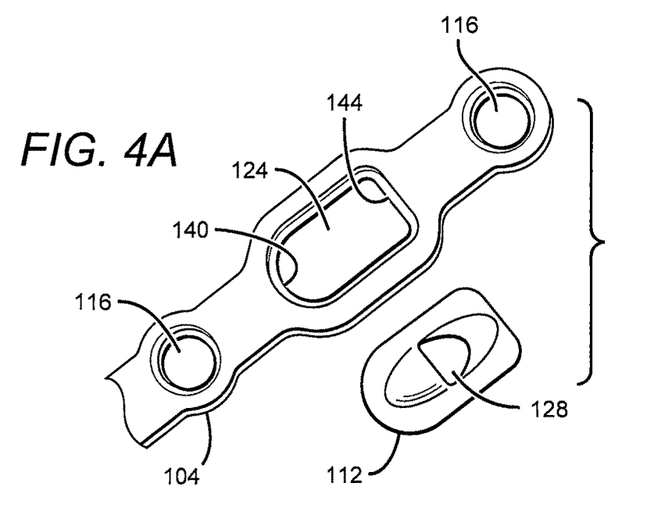
FIG. 4A illustrates an upper perspective view of an exemplary embodiment of a bone plate accompanied by a convertible insert for obliquely directing a fastener, according to the present disclosure.
Figure 4B:
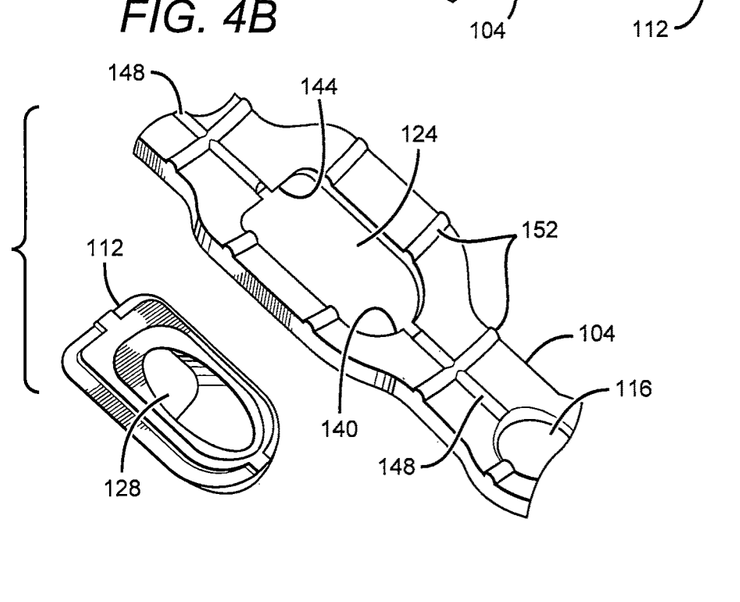
FIG. 4B illustrates a lower perspective view of the exemplary embodiment of FIG. 4A in accordance with the present disclosure.

FIGS. 1A-1B show the bone plate 104 with the convertible insert 112 installed into the insert aperture 124, such that the fastener 132 is directed at the oblique angle relative to the bone plate 104, as described above. Alternatively, FIGS. 2A-2B show an exemplary embodiment 134 of the bone plate 104 with the modular fixation insert 108 installed into the insert aperture 124. The insert 108 comprises a fixation aperture 136 configured to direct a fixation screw 120 at a substantially right angle relative to the bone plate 104, as best shown in FIG. 2A. It will be recognized that this insert 108 facilitates immobilizing adjacent bone parts. In some embodiments, the bone plate 104 and the insert 108 may be used with two or more fasteners 120 to fixate bones across a joint. It will be also appreciated that the fastener will have a smooth (non-threaded) so that lagging or compressing of bone fragments may be achieved.

In the embodiment illustrated in FIGS. 3A-4B, the insert aperture 124 comprises a countersunk edge which includes a round portion 140 and a flat portion 144 configured to orient and receive the inserts 108, 112. It will be appreciated that the round portion 140 and the flat portion 144 are configured to orient the inserts 108, 112 advantageously within the bone plate 104. In particular, the rounded portion 140 and the flat portion 144 orient the modular compression insert 112 such that the fastener 132 is directed along a majority of the length of the bone plate 104, thereby providing greater support to the fasteners 132 and the bones to be fixated. Further, each of the fixation apertures 116 comprises a countersunk surface configured to receive a head of the fixation screw 120, such that the fasteners 120 fixate the bone plate 104 to the bones.

In the embodiment of the bone plate 104 illustrated in FIGS. 3A-4B, the bone plate 104 comprises a longitudinal rib 148 and a multiplicity of lateral ribs 152. The ribs 148 and 152 serve to relieve stress on the bone plate 104 arising due to contact between the plate and the bones. The longitudinal rib 148 provides structural strength to the bone plate 104 so as to substantially inhibit bending along the length of the plate. The lateral ribs 152 support the contact at the longitudinal rib 148 and reduce contact between the plate and the bone.

Figure 5:
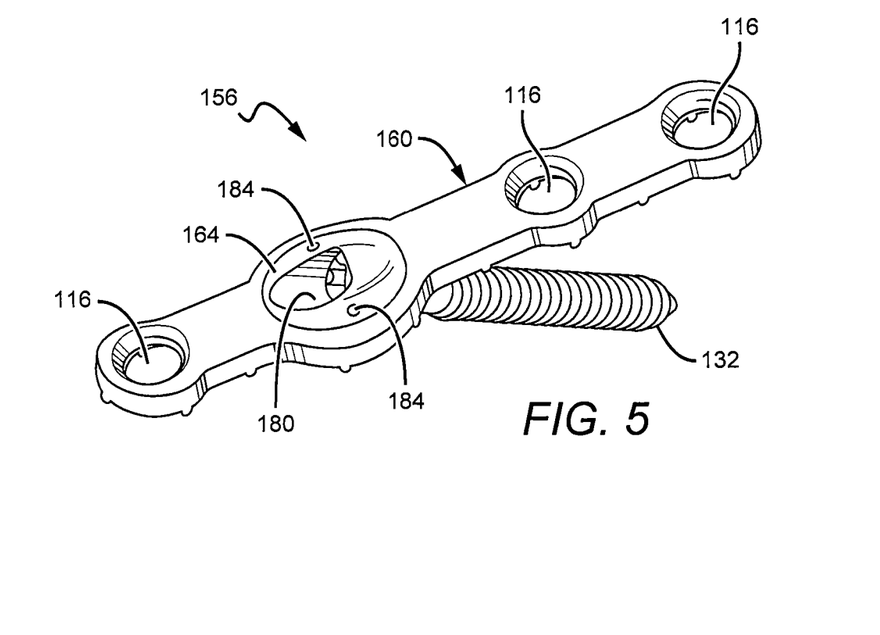
FIG. 5 illustrates an upper perspective view of an exemplary embodiment of a bone plate with a circular insert with an obliquely directed fastener, according to the present disclosure.
Figure 6:
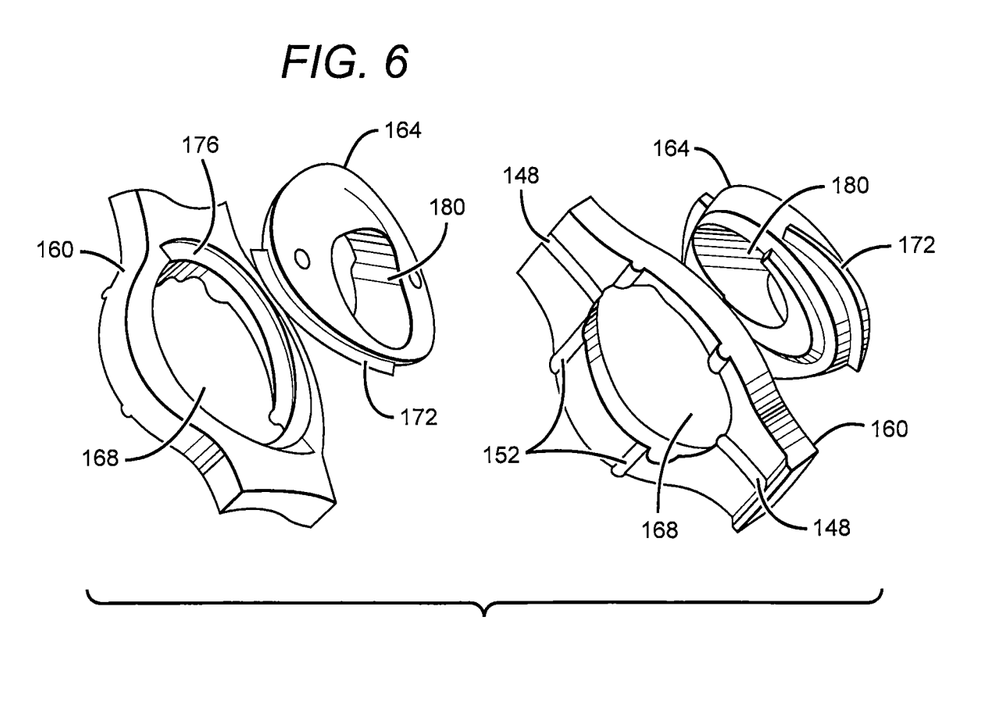
FIG. 6 illustrates an exploded view of a portion of the bone plate and the circular insert illustrated in FIG. 5, in accordance with the present disclosure.
Figures 7, 8:
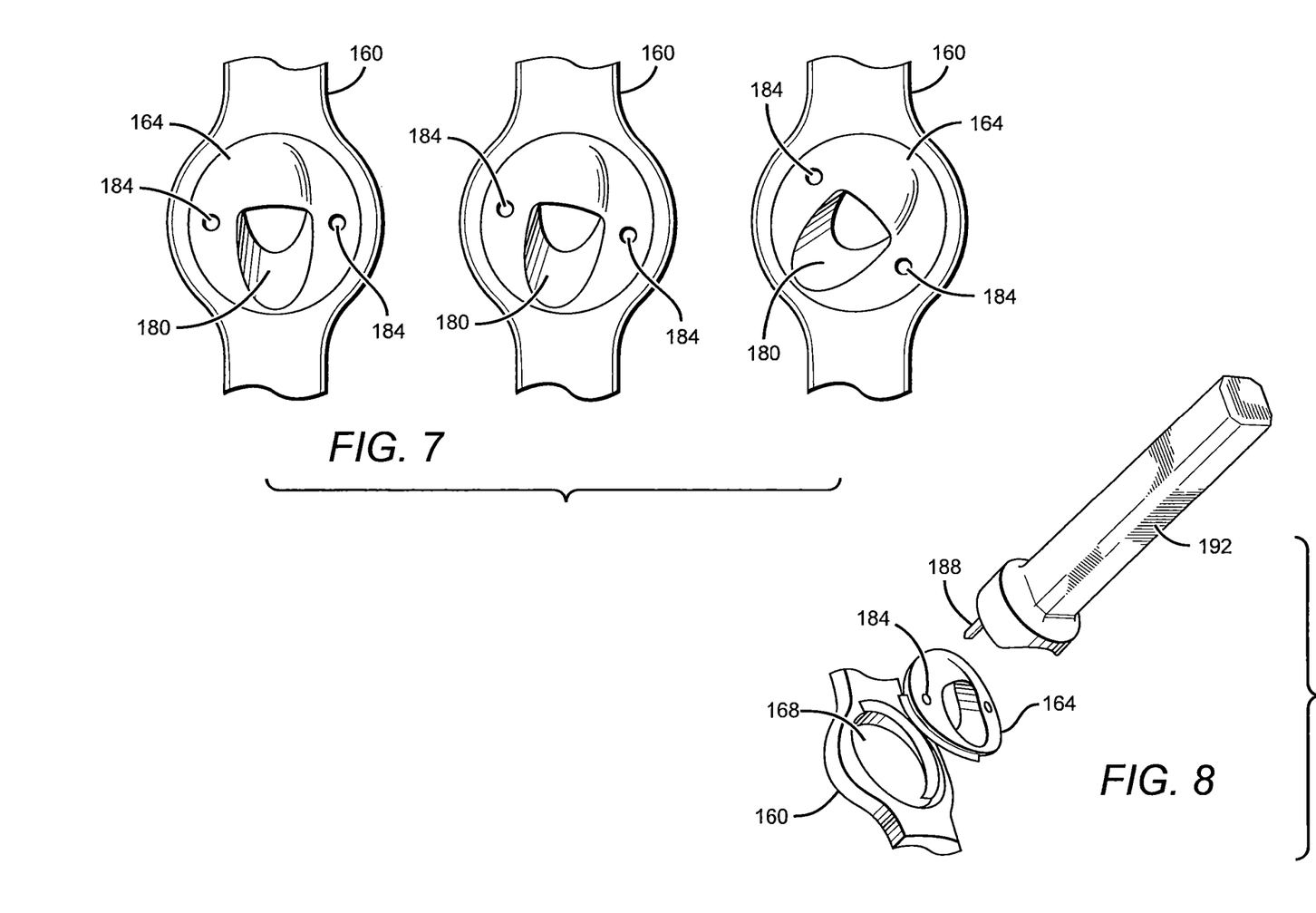
FIG. 7 illustrates top views of three different circular inserts of FIG. 5 that when secured to the same implant, direct fasteners in three different orientations rotated relative to the bone plate, according to the present disclosure.
FIG. 8 is an exploded view illustrating an exemplary embodiment of an insert driver configured to attach the circular insert to the bone plate illustrated in FIG. 5 in accordance with the present disclosure.
Figure 9:
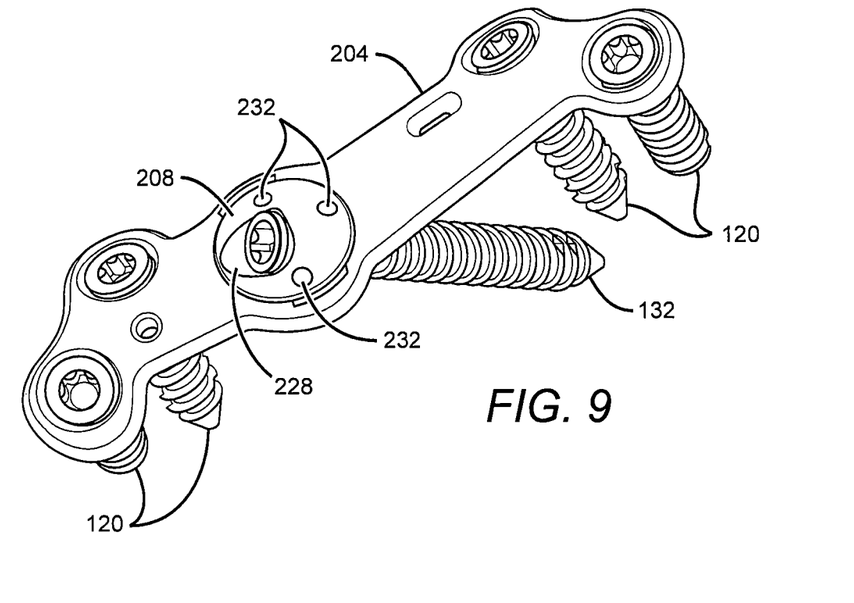
FIG. 9 illustrates an upper perspective view of an exemplary embodiment of a bone plate and a circular insert with an obliquely directed fastener, according to the present disclosure.
Figure 10:
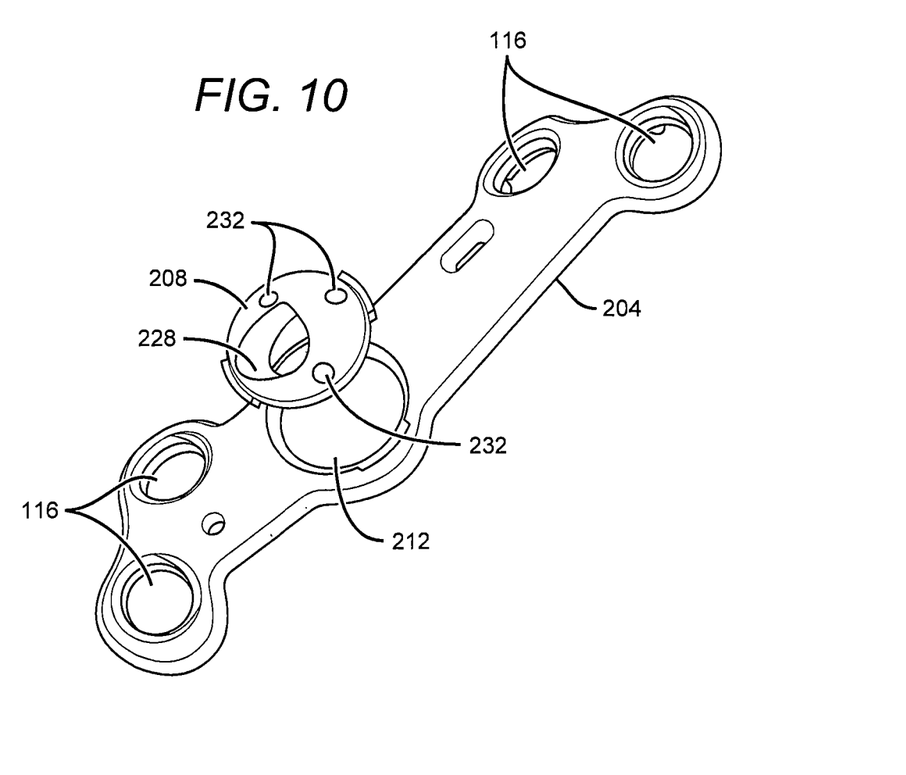
FIG. 10 illustrates an exploded view of the exemplary embodiment of the bone plate and the circular insert illustrated in FIG. 9, according to the present disclosure.

FIGS. 5-7 illustrate an exemplary embodiment 156 of a bone plate 160 coupled with a circular-shaped insert 164. The bone plate 160 is substantially similar to the bone plate 104, with the exception that the bone plate 160 comprises an insert aperture 168 which is configured to receive the circular insert 164. As best illustrated in FIG. 6, the circular insert 164 comprises threads 172 configured to rotatably engage with threads 176 of the insert aperture 168. As will be appreciated, the threads 172, 176 facilitate screwing the circular insert 164 into the insert aperture 168 and are configured to orient the circular insert relative to the bone plate for a desired fastener direction. In some embodiments, however, the circular insert 164 may be configured to be retained within the insert aperture 168, such as by way of the example, through an incorporation of recesses, tabs, notches, clips, various protruding formations, as well as various countersunk surfaces suitable for press-fitting the circular insert 164 into the insert aperture 168.

The circular insert 164 comprises an aperture 180 which is configured to receive the fastener 132, such that the fastener 132 is directed at an oblique angle relative to the plane of the bone plate 160. As described with reference to FIGS. 1A-2B, the oblique angle of the compression screw 132 facilitates compressing adjacent bones together so as to encourage bone fusion. Further, the circular insert 162, as well as the threads 172, 176, facilitates rotating the compression screw 132 relative to a longitudinal dimension of the bone plate 160, as illustrated in FIG. 7. In the embodiment illustrated in FIG. 7, the insert external threads 132 may be timed to orient the insert the fastener so that it is directed at an angle ranging between substantially 0 degrees and 360 degrees relative to the longitudinal dimension of the bone plate 160. It will be appreciated that the circular insert 162 and the threads 172, 176 facilitate directing the fastener 132 at various angles across a fusion site between adjacent bones. The fastener will have a smooth (non-threaded) so that a lagging or compressing of bone fragments may be achieved.

As best shown in FIGS. 5 and 7, the circular insert 164 comprises gripping holes 184. In the embodiment of FIGS. 5 and 7, the circular insert 164 comprises two gripping holes 184, although any number of gripping holes may be incorporated into the circular insert without deviating from the scope of the present disclosure. As best shown in FIG. 8, the gripping holes 184 are configured to receive one or more distal protrusions 188 of an insert driver 192. It should be understood that the insert driver 192 functions as a wrench, whereby the distal protrusions 188 may be engaged into the gripping holes 184 and then the insert driver 192 may be twisted so as to rotate the circular insert 164 within the insert aperture 168. It should be further understood, therefore, that the gripping holes 184 and the insert driver 192 facilitate directing the compression screw 132 at various angles across a fusion site between adjacent bones, as discussed with reference to FIG. 7.

FIGS. 9-13C illustrate an exemplary embodiment of a bone plate 204 coupled with a circular-shaped insert 208. The bone plate 204 is substantially similar to the bone plate 160, with the exception that the bone plate 204 comprises an insert aperture 212 which is configured to receive the circular insert 208. As best illustrated in FIGS. 12A and 12B, the circular insert 208 comprises circumferential protrusions 216 configured to rotatably engage with a groove 220 of the insert aperture 212. As will be appreciated, the circumferential protrusions 216 and the groove 220 facilitate engaging the circular insert 208 into the insert aperture 212 and are configured such that the circular insert may be positioned in various orientations relative to the bone plate. A countersink 224 within the insert aperture 212 maintains the circular insert 208 fastened within the bone plate 204. In some embodiments, however, the circular insert 208 may be configured to be retained within the insert aperture 212, such as by way of the example, through an incorporation of recesses, tabs, notches, clips, various protruding formations, as well as various countersunk surfaces suitable for press-fitting the circular insert 208 into the insert aperture 212, as described herein.

The circular insert 208 comprises an aperture 228 which is configured to receive the fastener 132, such that the fastener 132 is directed at an oblique angle relative to the plane of the bone plate 204. As described with reference to FIGS. 1A-2B, the oblique angle of the fastener 132 facilitates compressing adjacent bones together so as to encourage bone fusion. Further, the circular insert 208, as well as the circumferential protrusions 216 and the groove 220, facilitates directing the fastener 132 at an angle relative to a longitudinal dimension of the bone plate 204, as illustrated in FIGS. 13A and 13B. In the embodiment illustrated in FIGS. 9-13B, the circumferential protrusions 216 and the groove 220 are configured to orient the circular insert 208, and thus the fastener 132 at an angle ranging between substantially 0 degrees and 360 degrees relative to the longitudinal dimension of the bone plate 204. It will be appreciated that the circular insert 208, the circumferential protrusions 216, and the groove 220 facilitate directing the fastener 132 at various angles across a fusion site between adjacent bones. Moreover, the fastener 132 comprises a smooth, non-threaded portion, such that a lagging or compressing of bone fragments may advantageously be achieved.

Figure 11:
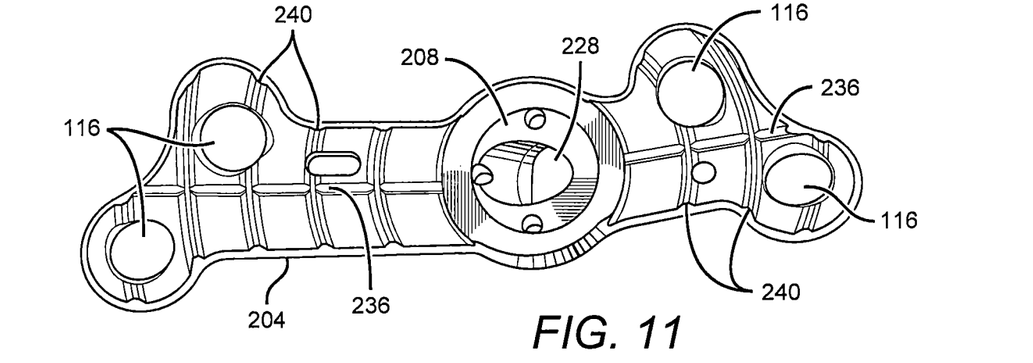
FIG. 11 illustrates a bottom view of the exemplary embodiment of FIG. 10 with the circular insert installed into the bone plate in accordance with the present disclosure.
Figure 12A:
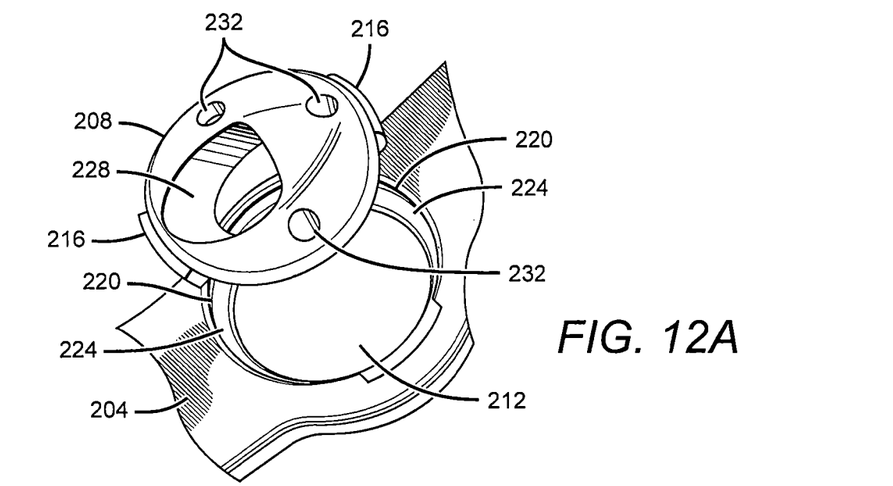
FIG. 12A illustrates an close-up exploded view of a portion of the bone plate and the circular insert illustrated in FIG. 10, according to the present disclosure.
Figure 12B:
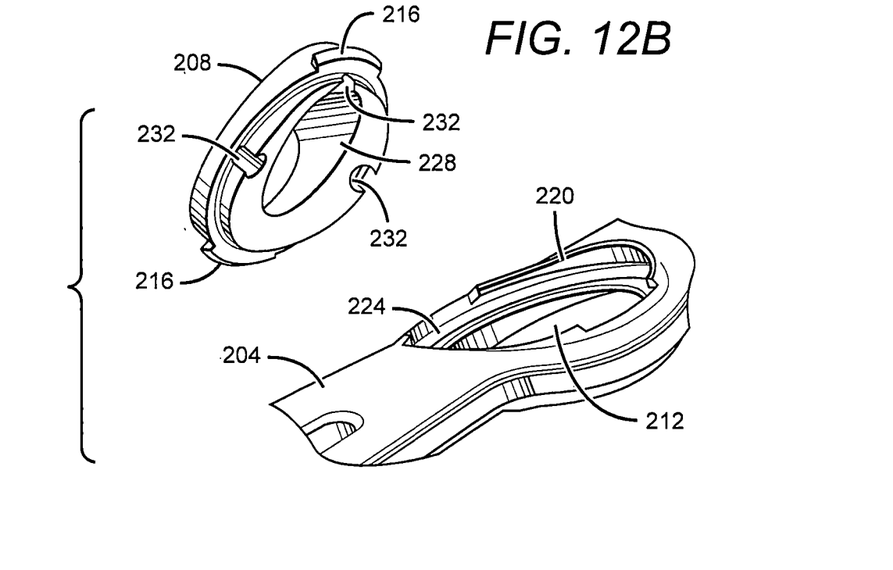
FIG. 12B illustrates an exploded view of an upper portion of the bone plate and a lower portion of the circular insert illustrated in FIG. 12A, according to the present disclosure.
Figure 13A:
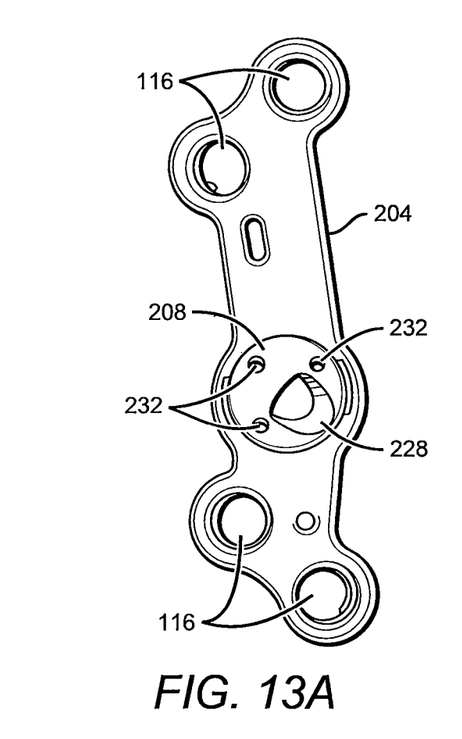
FIG. 13A illustrates a top view of an exemplary embodiment of a bone plate and a circular insert in an exemplary retaining position which directs a fastener in a rotated orientation relative to the bone plate in accordance with the present disclosure.
Figure 13B:
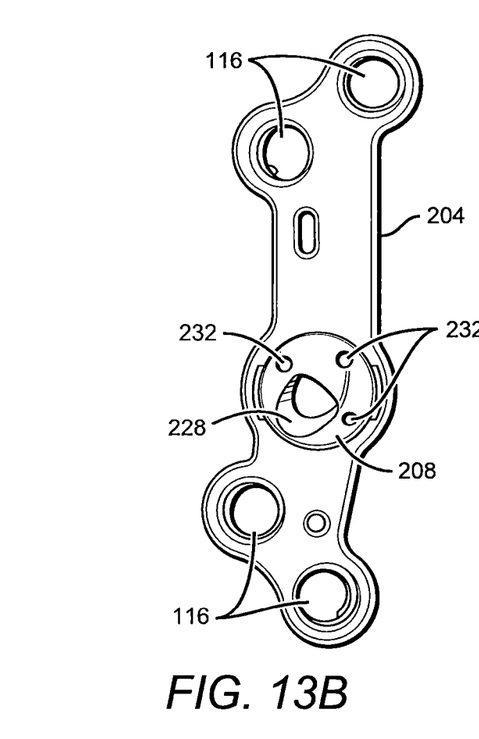
FIG. 13B illustrates a top view of an exemplary embodiment of a bone plate and a circular insert in an exemplary retaining position which directs a fastener in a rotated orientation relative to the bone plate, according to the present disclosure.
Figure 13C:
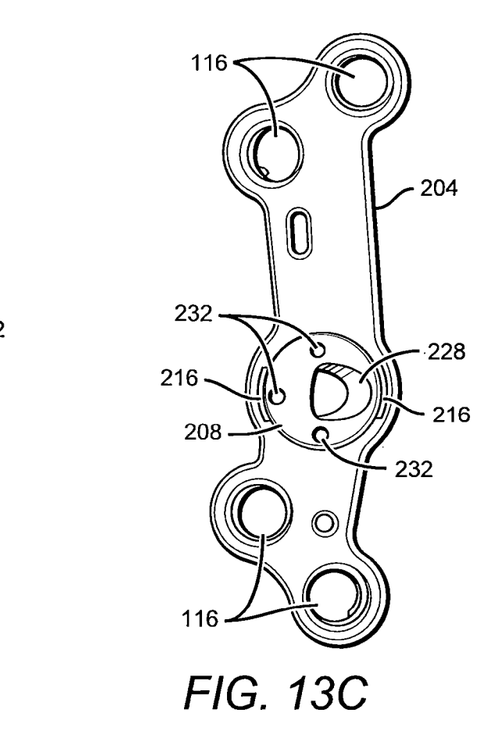
FIG. 13C illustrates a top view of an exemplary embodiment of a bone plate and a circular insert in an exemplary position which facilitates insertion and removal of the circular insert from the bone plate in accordance with the present disclosure.

As best shown in FIGS. 12A and 12B, the circular insert 208 comprises gripping holes 232. In the embodiment of FIGS. 9-13B, the circular insert 208 comprises three gripping holes 232, although any number of gripping holes may be incorporated into the circular insert without deviating from the scope of the present disclosure. It should be appreciated that the gripping holes 232 are substantially identical to the gripping holes 184, described above in connection with FIG. 8. As with the gripping holes 184, the gripping holes 232 are configured to receive one or more distal protrusions of a suitable wrench, such as the insert driver 192. The distal protrusions 188 may be engaged into the gripping holes 232 and then the insert driver 192 may be twisted so as to rotate the circular insert 208 within the insert aperture 212. It should be further understood, therefore, that the gripping holes 232 and the insert driver 192, or other suitable wrench, facilitate directing the fastener 132 at various angles across a fusion site between adjacent bones, as discussed herein.

As best illustrated in FIG. 11, the bone plate 204 comprises a longitudinal rib 236 and a multiplicity of radial ribs 240. The ribs 236 and 240 serve to relieve stress on the bone plate 204 arising due to contact between the plate and the bones. The longitudinal rib 236 provides structural strength to the bone plate 204 so as to substantially inhibit bending along the length of the plate. The radial ribs 240 support the contact at the longitudinal rib 236 and reduce contact between the plate and the bone. It will be appreciated that the longitudinal rib 236 is substantially similar to the longitudinal rib 236, extending along the longitudinal dimension of the bone plate 104. Further, the radial ribs 240 are substantially similar to the lateral ribs 152, with the exception that each of the radial ribs 240 comprises a circular segment having a radius of curvature. In some embodiments, the radial ribs 240 all have the same radius of curvature. In some embodiments, the radial ribs 240 each has a unique radius of curvature. In some embodiments, each of the radial ribs 240 has a unique radius of curvature extending from substantially the center of the circular insert 208, along the longitudinal rib 236, to the radial rib.

Moreover, it should be recognized that the bone plate 204 is not to be limited to flat plates, but rather the bone plate 204 may comprise curvature along the longitudinal dimension of the bone plate 204, curvature along a lateral dimension of the bone plate 204, as well as a combination of curvatures along the longitudinal and lateral dimensions of the bone plate 204. In some embodiments, the curvature may change along the longitudinal and lateral dimensions of the bone plate as a function of distance from the center of the insert aperture 212. In some embodiments, the curvatures along the longitudinal and lateral dimensions of the bone plate 204 are selected to match a specific surface topology of a bone to be treated. Accordingly, it should be understood that the bone plate 204 may be implemented with any combination of topological features without deviating from the spirit and scope of the present disclosure.

It is envisioned that the embodiments discussed herein may be coupled with various surgical instruments that are configured for implanting the bone plates, inserts, and fasteners into patients. In some embodiments, the surgical instruments may include without limitation, plate trials, wires, drills, drill guides, depth gages, cup and cone reamers, screw drivers, plate benders, and the like. It is further envisioned that the bone plates, inserts, accompanying fasteners, and the selected surgical instruments are to be suitably sterilized for surgeries and packaged into sterilized containers. In some embodiments, the insert and the bone plate may be packaged in an assembled state into a first sterile container, the fasteners may be packaged into a second sterile container, and the instruments may be packaged into a third sterile container. The first, second, and third sterile containers may then be bundled together into a single, exterior container, thereby forming a convenient surgery-specific bone fusion implant package. In some embodiments, however, the bone plate and the insert may be packaged into separate sterile containers, thereby allowing a surgeon to assemble the bone plate and the insert before or during surgery. It is envisioned that other packaging techniques will be apparent to those skilled in the art without deviating from the spirit and scope of the present disclosure.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A method for an apparatus for fusing bones of the human body, comprising:
   providing a semi-rigid biocompatible material for fusing two bone portions;
   forming the biocompatible material into a bone plate for contacting the two bone portions;
   providing fixation screws for fixating the bone plate to the two bone portions;
   configuring fixation apertures in the bone plate for orienting the fixation screws;
   forming a convertible insert for orienting a fastener to fuse the two bone portions; and
   configuring at least one insert aperture for retaining the convertible insert using a circular perimeter for supporting the convertible insert within the bone plate;
   wherein configuring the circular perimeter includes angling the fastener in an orientation across a fusion site between the two bone portions at an oblique angle relative to a plane of the bone plate and at an angle between substantially 0 degrees and 360 degrees relative to a longitudinal dimension of the bone plate; and
   wherein forming the convertible insert includes forming one or more engagement holes for receiving an insert driver for rotating the convertible insert within the at least one insert aperture.

2. The method of claim 1, wherein forming the biocompatible material into a bone plate includes configuring the bone plate to mate with the anatomy of the two bone portions.

3. The method of claim 1, wherein providing the semi-rigid biocompatible material includes providing a material that possesses a tensile strength suitable for fusing the two bone portions.

4. The method of claim 1, wherein forming the convertible insert includes configuring an aperture with any of a tapered, counter-bored, or countersunk internal shape for orienting the fastener in a direction for fixating or compressing the two bone portions.

5. The method of claim 4, wherein orienting the fastener comprises angling the fastener between substantially 0 degrees and 360 degrees relative to a longitudinal dimension of the bone plate.

6. The method of claim 4, wherein orienting the fastener comprises angling the fastener at an oblique angle relative to a plane of the bone plate.

7. The method of claim 1, wherein configuring the fixation apertures includes configuring the fixation apertures to engage with the fixation screws so as to fixate the bone plate to the two bone portions.

8. The method of claim 7, wherein configuring the fixation apertures includes configuring threads in any one or more of the one or more fixation apertures to retain a head of a fixation screw.

9. The method of claim 7, wherein configuring the fixation apertures includes configuring any one or more of the one or more fixation apertures to orient a fixation screw at a substantially right angle relative to the bone plate.

10. The method of claim 1, wherein configuring the at least one insert aperture comprises forming a countersunk edge to retain the convertible insert in the bone plate.

11. The method of claim 1, wherein configuring the at least one insert aperture comprises forming a perimeter comprising a round portion and a flat portion for supporting the convertible insert within the bone plate.

12. The method of claim 11, wherein forming the perimeter includes forming the round portion and the flat portion to cause the convertible insert to orient the fastener in a direction for fixating or compressing the two bone portions.

* * * * *